United States Patent [19]

Smith

[11] Patent Number: 5,173,287

[45] Date of Patent: * Dec. 22, 1992

[54] CARBOXYLIC ACID COMPOSITIONS

[76] Inventor: Walton J. Smith, P.O. Box 21, Lebanon, N.H. 03766

[*] Notice: The portion of the term of this patent subsequent to Jul. 23, 2008 has been disclaimed.

[21] Appl. No.: 713,854

[22] Filed: Jun. 12, 1991

Related U.S. Application Data

[63] Continuation-in-part of Ser. No. 472,389, Feb. 1, 1990, Pat. No. 5,034,416.

[51] Int. Cl.$^5$ .................. A61K 49/00; A61K 33/00; A61K 31/19

[52] U.S. Cl. ........................ 424/10; 424/715; 424/717; 514/557; 514/570

[58] Field of Search ............... 514/420, 557, 568, 569, 514/570; 424/715, 717, 10

[56] References Cited

U.S. PATENT DOCUMENTS 4,344,929  8/1982  Bonsen et al. .................. 514/427
4,990,530  2/1991  Takenaka et al. ............... 514/420

Primary Examiner—Frederick E. Waddell
Assistant Examiner—K. Weddington
Attorney, Agent, or Firm—Larson and Taylor

[57] ABSTRACT

A pharmaceutically acceptable composition comprising a biologically active acid compound or its salt and from one to five molar excess of a bicarbonate or carbonate.

3 Claims, No Drawings

CARBOXYLIC ACID COMPOSITIONS

This application is a continuation-in-part of U.S. application Ser. No. 07/472,389 filed Feb. 1, 1990, now U.S. Pat. No. 5,034,416.

This invention relates to improved carboxylic acid compositions and their use. More particularly it is concerned with compositions of carboxylic acids which have some useful biological activity and yet display some toxic effects.

It is an object of the present invention to provide a pharmaceutically acceptable composition comprising a biologically active carboxylic acid compound or its salt and a detoxifier for that compound.

This invention is an outgrowth of discoveries which I have made relating to biologically active carboxylic acids. The first discovery is that the inherent toxicity of this wide group of compounds is due to the neutralized acid. Previously, it had been thought that much or most of the activity of this group of compounds was due to the acid moiety in unneutralized form. Thus, I have discovered that much or most of the biological activity of these compounds is still present when neutralized or in salt form.

My second discovery in this connection was that much of the biological activity of salts of carboxylic acids could be noneffective or neutralized by bicarbonate ions without altering the pH of the carboxylic acid salt.

I have taken advantage of these two major discoveries in developing methods of detoxifying carboxylic acid salts which is the subject of this invention.

So that this invention be better understood, I shall enlarge on these discoveries and further describe this invention.

I have used a variety of test methods to confirm the benefits of this invention. This includes animal studies, however, the basic discovery was made with plants.

DISCOVERY OF THE ACTION OF CARBOXYLIC ACIDS

It should be kept in mind that virtually all tissues are neutral, with slight variations. No matter in what form the carboxylic acid is administered, when it reaches the blood stream, it is in salt form at the same pH as the blood.

I have used germinating seedlings for studying the mechanism of a wide variety of water soluble substances. Under very controlled conditions, I can study the various mechanisms in the seedlings by studying the growth with a substance, such as carboxylic acid salt, and making a comparison with that combining the salt with another substance.

These studies have been going on for several decades under my direction, and more than 4,700 separate experiments involving tens of thousands of man hours. The biochemical mechanisms in plants are more readily studied because they are not subject to many of the variables present in animals which often have nothing to do with the subject under investigation. Since plants had to precede animals and humans in the evolution of this planet: it is not surprising that the basic biochemistry is similar and often identical. Animals and humans could not exist with a food source, which plants provided.

This invention is also an outgrowth of my discovery concerning the relationships between chemicals, and how this in turn has an effect on biochemical reactions, and eventually on growth.

I have discovered that the relationship between chemicals in a bio chemical system is often a major factor in the process of growth. Calcium ions, as an example, have a simple antagonistic relationship with ions such as fluoride and lithium. These ions inhibit growth of seedlings and this may be reversed with calcium.

I refer to these relationships as "Chemicals vs. Chemicals". They are abundant in living systems, and they are separate from the relationships between chemicals and enzymes.

In addition I have discovered that germinating seedlings may be used to advantage to discover the nature of these relationships. I have discovered that such studies in germinating seedlings are the equivalent of a study using animal embryos, the use of which is hardly practical. It is primarily studies using these plant embryos which permitted the discoveries outlined in this application.

Accordingly, I have discovered that there is an antagonistic relationship between the salts of most organic carboxylic acids and bicarbonate ions. It is this discovery which is the essence of this invention.

Both carboxylic acids and bicarbonate ions exist in plants and most living things. Bicarbonate is a major ingredient of blood and besides controlling pH, it enters into many reactions which result in components of all cells. Carboxylic acids also exist in most living things. Acetate is a building block for many of the chemicals in the body, and amino acids are the building blocks for proteins.

Since I have found an antagonism between bicarbonate ions and many carboxylic acids, it is important to ascertain where this antagonism can be utilized, and this is the subject of this patent application.

In the course of my investigation, I have found that acids such as salicylic acid inhibit the growth of germinating seedlings. There is some variation in the degree of inhibition, and I have used neutralized acids (salts) in my studies to eliminate the role of pH. In the beginning the principal interest was in Salicylates and Aspirin which are known to cause bleeding in GI tracts along with more permanent damage. As reported previously I have found that this damage can be prevented with simultaneous administration of bicarbonate.

Not only are there a wide variety of analgesics which respond favorably to bicarbonate, but there are many other acids used in pharmacology which benefit by the combination with bicarbonate. Below is a partial list of a few of the acids which in my experiments I have found to inhibit the growth inhibition due to the acid group:

Calcium Lactate
Sodium Propionate
Pivalic Acid, Na salt
Alpha Dimethyl Valerate
Sodium Valproate
Sodium Caproate
Sodium Undecylenate All the above aliphatic acids are strong inhibitors of growth, and much of the inhibition can be reversed with bicarbonate. Some of the compounds have pharmaceutical applications. Sodium Valproate, for example, is used routinely in the treatment of certain mental disorders (spasms & fits). The toxicity is often so great that many young children are not able to take the drug. It is therefore desirable to reduce its toxicity.

Among aromatic analgesics, the following compounds were found to show a toxicity reduction with bicarbonate:
Sodium Flubiprofen
Sodium Indomethacin
Sodium Fenclofenac
Sodium Diclofenac
Piroxicam
Sodium Zomepirac
Additional aromatic compounds whose toxicities are reduced with bicarbonate are:
Sodium Diphenylacetate
Sodium 2,2'-Iminodibenzoate
Sodium Phenoxyacetate
Sodium Phenylpropionate
Gemfibrozil Besides the fact that the growth inhibitions and resultant toxicities of the salts of acids are reduced by bicarbonate salts, I have made some studies to explain the role of bicarbonate. I have found that some of the toxicity of many of these acids can be overcome to some degree with some members of the citric acid cycle including Salts of Fumaric acid, Succinic acid, Citric acid, and Formic acid. They may be used instead of bicarbonate salts, but are usually less effective.

It should be noted that the above list is only a partial list of compounds which I have studied and found to be sensitive to the action of bicarbonate. I have discovered that even compounds such as Deoxycholic acid shows a favorable (as the salt) response to bicarbonate.

It can be seen that the toxicity of a wide variety of carboxylic acids may be ameliorated by combining the substance with a soluble bicarbonate i a dosage form. It can also be seen that a dosage form utilizing the carboxylic acid as a salt, soluble or less soluble, puts less of a burden on the dosage form to neutralize the acid in the intestinal tract wasting some of the bicarbonate present. It can also be seen that the use of enteric coating in a more sophisticated manner helps the dosage form still more.

It may be wise to differentiate the use of bicarbonates and carbonates. This invention requires the presence of a soluble bicarbonate to be effective. Soluble carbonates naturally are useful since they become bicarbonate in the presence of acid, and they are useful in dosage forms to reduce their size when there is stomach acid to be neutralized as well. This is also true to some extent of insoluble carbonates such as calcium and magnesium carbonates which are useful in reducing the amount of stomach acid that is available to destroy the bicarbonates present, but they are not as useful otherwise in accomplishing this invention in that their bicarbonates are unstable or non existent. Nevertheless, this invention visualizes a degree of usefulness for insoluble carbonates and emphasizes the value of soluble bicarbonates.

We have confirmed that the carbonate may be in several forms and still be useful for accomplishing this invention, and an example of one useful form would be exemplified by the substance Dihydroxyaluminum Sodium Carbonate. This invention may be accomplished by taking a bicarbonate along with the biologically active drug or often just after taking the drug.

I claim:

1. A pharmaceutically acceptable composition comprising Flubiprofen or its salt and from one to five molar excess of a bicarbonate or carbonate.

2. A pharmaceutically acceptable composition comprising Gemfibrozil or its salt and from one to five molar excess of a bicarbonate or carbonate.

3. A pharmaceutically acceptable composition comprising Valproic or its salt and from one to five molar excess of a bicarbonate or carbonate.

* * * * *